United States Patent
Stangel et al.

(10) Patent No.: US 6,664,245 B2
(45) Date of Patent: Dec. 16, 2003

(54) ADHESIVE COMPOSITIONS FOR HARD TISSUES

(75) Inventors: Ivan Stangel, Bethesda, MD (US); Jingwei Xu, Quebec (CA); Thomas Ellis, Montreal (CA); Edward Sacher, Quebec (CA)

(73) Assignee: BioMat Sciences, Inc., Rockville, MD (US)

(*) Notice: Subject to any disclaimer, the term of this patent is extended or adjusted under 35 U.S.C. 154(b) by 0 days.

(21) Appl. No.: 10/339,621

(22) Filed: Jan. 10, 2003

(65) Prior Publication Data

US 2003/0118523 A1 Jun. 26, 2003

Related U.S. Application Data

(60) Division of application No. 09/785,555, filed on Feb. 20, 2001, which is a continuation-in-part of application No. PCT/US99/18582, filed on Aug. 17, 1999.
(60) Provisional application No. 60/096,838, filed on Aug. 18, 1998.

(51) Int. Cl.$^7$ ............................ A61K 31/661; C07F 9/09
(52) U.S. Cl. ..................... 514/112; 558/183; 558/303; 514/129
(58) Field of Search ................... 558/183, 303; 514/112, 129

(56) References Cited

U.S. PATENT DOCUMENTS

| 3,449,303 A | 6/1969 | Caldwell et al. |
| 4,499,251 A | 2/1985 | Omura et al. |
| 4,514,342 A | 4/1985 | Billington et al. |
| 4,657,941 A | 4/1987 | Blackwell et al. |
| 4,719,149 A | 1/1988 | Aasen et al. |

FOREIGN PATENT DOCUMENTS

| JP | A-7-185291 | 7/1995 |
| JP | A-9-286851 | 4/1997 |
| JP | A-11-21319 | 1/1999 |

*Primary Examiner*—Alan L. Rotman
*Assistant Examiner*—Golam M M Shameem
(74) *Attorney, Agent, or Firm*—Fitch, Even, Tabin & Flannery

(57) ABSTRACT

An adhesive composition is provided which is suitable for the bonding of polymeric materials, in whole or in part, such as composite resins, or methacrylate-containing glass-ionomer filling materials, to tooth enamel, or tooth dentin, or to other hand tissues of the human body, such as bone. The composition comprises an unsaturated carboxylic acid ester, an unsaturated phosphate ester and other crosslinking agents. The especially preferred phosphates (which are provided as new compounds) are those of formula (I) in which: $R_1$ is a hydrogen atom, alkyl $C_1$–$C_4$, or CN; R is an aliphatic, cycloaliphatic or aryl radical containing from 1 to 10 carbon atoms and having a valence of n+1; n is an integer from 1 to 5, preferably from 3 to 5.

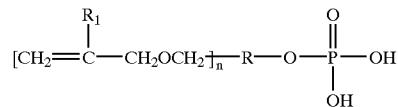

13 Claims, No Drawings

ADHESIVE COMPOSITIONS FOR HARD TISSUES

RELATED APPLICATIONS

This is a divisional application of U.S. application Ser. No. 09/785,555, now allowed filed Feb. 20, 2001, which is a continuation-in-part of and claims the benefit of PCT Application PCT/US99/18582, filed Aug. 17, 1999, which designated the United States and claims the priority benefit of U.S. Provisional Application No. 60/096,838, filed Aug. 18, 1998, the disclosures of which are incorporated by reference.

BACKGROUND OF THE INVENTION

1. Field of the Invention

This invention relates to adhesive compositions, especially those which are suitable for promoting the bonding of dental restorative materials, especially those that have polymeric components, to tooth enamel, or to tooth dentin or other hard tissues of human body, such as bone. The restorative materials can be polymers, or resins, or can contain polymers or resins in whole, or in part, and comprise materials such as dental composite resins, or methacrylate containing glass ionomer filling materials, or glass ionomer filling materials having ethylenically unsaturated bonds, or they can comprise resin cements.

2. Background of the Invention

The bonding of restorative materials to tooth structure has been an important goal of the dental profession. Such bonding has the benefits of (1) efficiently retaining materials to tooth structure without the need for mechanically locking filling materials into teeth, the latter being a procedure which requires the removal of otherwise healthy tooth structure, and which has been the historical way that materials have been retained, (2) simplifying treatment procedures by eliminating the need for forming precise geometric shapes of teeth when surgical interventions are made, (3) enhancing the quality of interfaces between filling materials by improving the seal between tooth structure and filling materials.

Filling materials in dentistry are generally used to restore teeth to form and function, as well as seal the tooth against oral fluids and bacteria. Directly filling materials are those that are placed in a tooth, and then hardened in the tooth. The most commonly used direct filling polymeric materials are polymer-matrix composite resins, and resin-containing or resin modified glass ionomer filling materials. Compositions for bonding these polymeric materials to tooth structure are especially useful.

Composite resins general comprise a resin matrix, an inorganic filler phase and some coupling agents. The resin matrix generally comprises a monomer system, an initiator system and other stabilizers. The monomer system comprises unsaturated compounds. These compounds generally comprise one or more esters of ethylenically unsaturated carboxylic acids and the adduct of bisphenol A and glycidyl methacrylate (Bis-GMA), such as triethyleneglycol dimethacrylate (TEGDMA), ethyleneglycol dimethacrylate (EGDMA) and 2,2-bis-[4-(2-hydroxy-3-methacrylyloxypropoxy)phenyl]-propane ether (Bis-GMA) in U.S. Pat. No. 3,066,112 to Bowen. Another class of unsaturated materials are urethane dimethacrylates, such as the 1,6-bis(methacrylyloxy-2-ethoxycarbonylamino-2,4,4-trimethylhexane (UEDMA) which is synthesized from 2-hydroxyethyl methacrylate and 2,4,4-trimethylhxamethylenedisocynanate.

When composite resins are placed in a tooth cavity and cured, the hardening ("polymerization") of the material usually results in shrinkage. This shrinkage leads to marginal gap formation, allowing for the passage of fluid, bacteria, molecules or ions between the restoration and the cavity wall, which may result in secondary caries, marginal discoloration and pulpal damage. The longevity of the restoration will be reduced by this micro-shrinkage. A strong and permanent bond between the wall of the cavity and the restorative will lead to good sealing, and is beneficial.

Bonding to dental surfaces is usually achieved by the use of acid conditioners, primers and adhesive resins. Primers, which can be applied sequentially, or simultaneously with adhesive resins, generally contain one or more polar groups and unsaturated groups. It is assumed that the polar groups will bond either to the inorganic crystal lattice (apatite) portion of tooth structure, or to the polar part of collagen in the tooth, this occurring by chemical or hydrogen bonding, and/or by micromechanical retention due to the formation of a hybrid layer. The hybrid layer, which has been well characterized, is formed by the infiltration of the primer into a demineralized dentin zone, the demineralization having resulted from acid etching of the tooth. The unsaturated groups of the primer will bond with resin overlayers by free radical polymerization. The polar groups are normally a phosphate, an amino acid or amino alcohol, or a dicarboxylic acid.

U.S. Pat. No. 4,368,043 to Yamauchi, incorporated herein by reference, discloses an adhesive cementing agent for the human body. This agent contains a phosphoric or phosphonic acid ester compound, or a high molecular weight compound obtained by polymerizing the compound whether alone or as co-monomer units.

U.S. Pat. No. 4,514,342 to Billington, incorporated herein by reference, describes an adhesion promoter, suitable for improving the adhesion of composite dental material to tooth enamel. This adhesion promoter contains volatile organic solvent and a polyethylenically unsaturated monophosphate or salt, which contains a monophosphate radical and at least three ethylenically unsaturated groups.

A biologically compatible adhesive is disclosed in U.S. Pat. No. 4,657,941 to Blackwell, incorporated herein by reference. This adhesive is shelf stable as a single component adhesive and includes a mixture of an adhesive promoting and polymerizable monomer system. A free radical polymerizable monomer or prepolymer having ethylenic unsaturation and a phosphorus-containing adhesion promoter, having a free radical polymerization catalyst and an accelerator for the catalyst are included in this system.

While the adhesion between filling materials and enamel or dentin of the tooth is improved by usage of an adhesive promoter, some disadvantages, such as not having great bonding strength, or too great a viscosity for handling of some component exists in some adhesives.

SUMMARY OF THE INVENTION

An object of this invention is to provide an adhesive composition, which is suitable for promoting the adhesion of restorative materials to tooth enamel, tooth dentin or other hard tissues of human body.

It is a further object of this invention to provide an adhesive composition which is suitable to be used with other hard tissues of the body.

It is a further object of this invention to provide an adhesive composition, which, when used with other resins, can seal dentinal tubules.

This composition contains a volatile organic solvent and an ethylenically unsaturated monomer and phosphate, which contains a mono-, or di-phosphate radical and at least three ethylenically unsaturated groups.

The preferred solvent is a lower aliphatic alcohol and carbonyl compound. The solution is preferably from 1 to 50% by weight of the total solution of ethylenically unsaturated monomer and phosphate.

The ethylenically unsaturated monomer in the composition is a mono-, di, tri, or multifunctional acrylic monomer, such as 2-hydroxyethyl methacrylate, 1,3-butanediol dimethacrylate, 1,4-butanediol dimethacrylate, or 1,4-butanediol divinyl ether.

The ethylenically unsaturated phosphate is the reaction product of alcohol containing unsaturated allyl ether and phosphorus oxychloride or other phosphorus containing compounds.

A very important aspect of this invention are the novel compounds are represented by following formula:

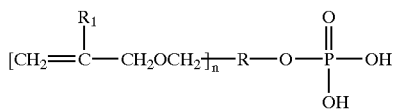

in which:

R$_1$, is a hydrogen atom, alkyl C$_1$–C$_6$, (preferably C$_1$–C$_4$ when alkyl), or CN, R is an aliphatic, cycloaliphatic or aryl radical containing from 1 to 10 carbon atoms and having a valence of n+1, n is an integer from 1 to 5, preferably from 3 to 5, which can be used as a primer for hard tissues.

DETAILED DESCRIPTION OF THE INVENTION

It has been found, in accordance with the present invention, that the adhesion of filling materials to enamel; or to dentin, may be considerably improved by first applying the composition of this invention to prepared dentin or enamel. The preparation procedure can involve the application of an acid to the tooth surface (where bonding is required), a technique which is known as acid-etching, and which is well known in the dental art. On enamel, the treatment of tooth surfaces with acid preferentially removes inter-rod material, and creates micropores into which the invention, in combination with other resins, can penetrate to form mechanical anchors (tags), when hardened. On dentin, the acid dissolves the mineral phase of dentin, and exposes a fibrillar network of collagen. It is believed that the adhesion results from the penetration of the said composition into the exposed collagen network, and subsequent hardening of the said composition in conjunction with other resins placed as overlayers. These overlayers (known as intermediary resins, or adhesive resins) bond with restorative materials or cements which are subsequently placed on the overlayers.

The adhesive composition, in accordance with this invention, consists of a volatile organic solvent and an ethylenically unsaturated monomer and phosphate, which contains a mono-, or di-phosphate radical and at least three ethylenically unsaturated groups.

The preferred solvent is a lower aliphatic alcohol and carbonyl compounds. The most preferred solvent is acetone. The concentration of the solvent in solution is from 1 to 90% by weight of the total solution of ethylenically unsaturated monomer and phosphate, preferably from 10 to 80% of the total solution of ethylenically unsaturated monomer and phosphate, and most preferably from 30 to 70% by weight.

The ethylenically unsaturated monomer in the composition is a mono-, di, tri, or multifunctional acrylic monomer, such as 2-hydroxyethyl methacrylate, 1,3-butanediol dimethacrylate, 1,4-butanediol dimethacrylate, or pentaerythritol triacrylate. The most preferred monomer is 2-hydroxyethyl methacrylate. The concentration of monomer in the composition is from 1 to 60% by weight. The preferred concentration is from 20 to 50% by weight, and the most preferred concentration is from 30 to 40% by weight.

The ethylenically unsaturated phosphate is a reaction product of alcohol containing unsaturated allyl ether and phosphorus oxychlonde or other phosphorus containing compounds.

The unsaturated allyl ether in the phosphate are preferably vinyl groups.

The introduction of phosphate in the composition is very important. It is presumed that the phosphate will interact with inorganic components of a tooth, or other hard tissues, either by forming a complex with the calcium ion or forming a chemical or hydrogen bond with the phosphate, with mineral in enamel, or with mineral that is left in dentin after etching. The phosphate may also be important for interacting with collagen. A very important aspect of this invention is that the new compounds have the following formula:

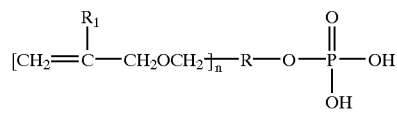

in which:

R$_1$, is a hydrogen atom, alkyl C$_1$–C$_4$ or alkyl C$_1$–C$_6$, or CN,

R is an aliphatic, cycloaliphatic or aryl radical containing from 1 to 10 carbon atoms and having a valence of n+1, n is an integer from 1 to 5, preferably from 3 to 5.

The preferred concentration of phosphate in the composition is from 2 to 70% by weight, although in principle useful results are obtainable in a range of 2–17% by weight. In another aspect, a range of 5 to 40% by weight can be used. The most preferred is from 5 to 10% by weight.

A solution containing the phosphate compound and which is applied to a tooth surface can be hardened simultaneously with resin overlayers which already contain hardening agents. The solution of PTEPAE can also be hardened by the addition of known hardening agents, such as camphorquinone, or benzoyl peroxide.

The invention will be understood by the following examples, which are given by way of illustration only:

EXAMPLE 1

Pentaerythritol Triallyl Ether Monophosphate Acid Ester (PTEPAE)

A solution containing phosphorus oxychloride (15.3 g) in dry ether (60 ml), or methyl ter-butyl ether, isopropyl acetate, di-isopropyl ether, but preferably dry ether, was slowly dropped into a solution containing technical pentaerythritol triallyl ether (9.9 g) and triethylamine (3.8 g) in dry ether (60 ml) at 0° C. The solution is stirred for 16 hours at room temperature. The precipitation of the triethylamine hydrochloride is filtered off, and the solution is hydrolyzed by the addition of the ether solution into ice water (100 ml)

with stirring. The mixture is separated, and the ether layer is basified with sodium carbonate solution to obtain a pH=10, and then acidified with hydrochloric acid to obtain pH=4. The ether layer is extracted and dried by magnesium sulphate. The ether is extracted under reduced pressure to give the title compounds as a clear colorless liquid. The $H^1$ NMR spectrum of this compound shows peaks around 6.2–5.8, 5.6–5.1, 4.5–4.1, 4.0–3.8, 3.6–3.4, 2.2–2.0 1.5–1.2, 1.0–0.8 ppm.

EXAMPLE 2

Five solutions each containing acetone and one of the following primers: pentaerythritol triallyl ether (PTE) (10% by weight), PTEPAE (10% by weight), 2-hydroxylerhyl methacrylate (HEMA) (35% by weight), a mixture of HEMA (35% by weight) and PTEPAE (10% by weight), or a mixture of HEMA (35% by weight) and PTE prior listed percentages, with the balance being acetone. Maleic acid was dissolved into water to obtain a pH=0.8, although other acids such as phosphoric acid, citric acid, or nitric acid, having a pH ranging from of 0.5 to 4.0, most preferably from 0.8 to 3.0, can be used. Bond strength for each of the solutions was determined. For the bond strength test, the occlusal enamel of extracted caries-free human teeth was removed with a rotating diamond blade using a copious amount of water to expose the dentin surface. The sectioned teeth were mounted in PVC rings using polymethyl-methacrylate with the dentin surface being 0.5 mm above the edge of the ring. The mounted teeth were ground with a Buehler Metaserv Grinder (Buehler LTD, U.K.) using 1200-grit paper at 150 rpm and 5 psi until a uniformly reflective, smooth, and flat dentin surface appeared. Multiple layers of the priming solution were placed on the dentin surface. Note that, as part of the method, it is important to place multiple layers of the adhesive on the surface so that after said etching, full saturation of the demineralized layer by the priming solutions occur. After the primers were placed, a commercial intermediary resin, D/E resin (BISCO, Itasca, Ill., USA. Reorder No. B-2502A) and AELITEFIL composite (BISCO, Itasca, Ill., USA. Lot No. 089226) were sequentially placed on the surface of dentin according to the procedure described in the reference Stangel et al., Journal of Adhesion, Vol. 47, p.p. 133–149,1994, incorporated herein by reference in its entirety. After 24 hours storage in water, all samples were loaded on Instron Series IX Automated Materials Testing System, and tested to failure at a cross-head speed oft nzm/minute. The results are shown in TABLE 1.

TABLE 1

Bond Strength of composite resin to dentin

| Primer Composition | Acid Treatment of Dentin | Average Peak Stress (MPa) | Number of samples |
| --- | --- | --- | --- |
| PTE | no etch | 5.0 | 10 |
| PTEPAE | no etch | 6.5 | 8 |
| PTEPAE | Etched | 1.8 | 7 |
| HEMA | Etched | 12.1 | 5 |
| HEMA + PTEPAE | Etched | 19.9 | 12 |
| HEMA + PTE | Etched | 9.0 | 6 |

EXAMPLE 3

A mixture of 2-hydroxylethyl methacrylate (HEMA) (35% by weight) and PTEPAE (10% by weight), the balance being acetone, was prepared. Samples for testing the bond strength of the solution to dentin were prepared as described in example 2. The samples were immersed in a water bath at 37° C. for 24 hours, and tested to failure as described in Example 2. The mean peak stress at failure, for seven samples was 20.5 MPa.

EXAMPLE 4

A mixture of 2-hydroxylethyl methacrylate (HEMA) (35% by weight) and PTEPAE (10% by weight), the rest being acetone was prepared. Samples for testing the bond strength of the solution to dentin were prepared as described in example 2, except the dentin was etched by phosphoric acid having a concentration of about 35% (by weight). The samples were immersed in a water bath at 37° C. for 24 hours, and tested to failure as described in Example 2. The mean peak stress at failure, for six samples was 25.5 MPa.

EXAMPLE 5

A mixture of 2-hydroxylethyl methacrylate (HEMA) (35% by weight) and PTEPAE (10% by weight), the rest being acetone was prepared. Samples for testing the bond strength of the solution to dentin were prepared as described in Example 2. The samples were immersed in a water bath at 100° C. for two hours, and tested to failure as described in Example 2. The mean peak stress at failure, for eight samples was 17.3 MPa.

EXAMPLE 6

A flat surface of bovine enamel was placed in a bedding of polymethylmethacrylate as described for dentin samples in Example 2. The surface of the enamel was etched with phosphoric acid having a concentration of about 35% (by weight). The surface was then treated with a solution consisting of a mixture of 2-hydroxylethyl methacrylate (HEMA) (35% by weight) and PTEPAE (10% by weight), the rest being acetone. After allowing the acetone to evaporate, a solution consisting of a 1:1 mixture of bisphendl-A glycidyl methacrylate (Bis-GMA) and triethyleneglycol dimethacrylate (TEGDMA) was applied. Composite resin was positioned on the surface, and the materials were hardened by exposure to a visible light. After 24 hours storage in water, the samples were tested to failure as described in Example 2. The mean peak stress at failure, for seven samples was 18.0 MPa.

What is claimed is:
1. A method of treating a tooth employing the steps of:
   etching a tooth surface;
   applying a composition in multiple layers on the etched moth, said composition comprising a 2-hydroxylethylmethacrylate and an ethylenically unsaturated monophosphate represented by the formula:

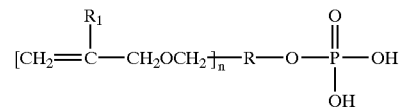

in which:
   $R_1$, is a hydrogen atom, alkyl $C_1$–$C_4$, or CN,
   R is an aliphatic, cycloaliphatic or aryl radical containing from 1 to 10 carbon atoms and having a valence of n+1,
   n is an integer from 1 to 5; and
   applying a resin overlayer.

2. A method of clam 1, wherein said composition and a resin overlayer are simultaneously applied.

3. A method of claim 1, wherein the multiple layers are 3 to 15.

4. The method of claim 1, wherein said ethylenically unsaturated monophosphate is pentaerythritol trimethyl ether monophosphate acid ether.

5. The method of claim 1, wherein n is from 3 to 5.

6. The method of claim 1, wherein R represents a cycloaliphatic radical.

7. The method of claim 1, wherein R represents an aryl radical.

8. The method of claim 1, wherein n is greater than 1.

9. The method of claim 6, wherein n is greater than 1.

10. The method of claim 7, wherein n is greater than 1.

11. The method of claim 5, wherein R is selected from the group consisting of a cycloaliphatic radical and an aryl radical.

12. The method of claim 1, wherein the multiple layers are 3 to 15.

13. The method of claim 12, wherein R is selected from the group consisting of a cycloaliphatic radical and an aryl radical.

* * * * *